(12) United States Patent
Shim et al.

(10) Patent No.: US 11,181,468 B2
(45) Date of Patent: Nov. 23, 2021

(54) SIGNAL DETECTION SENSOR, APPARATUS AND METHOD FOR ANALYZING COMPONENT OF OBJECT

(71) Applicant: SAMSUNG ELECTRONICS CO., LTD., Suwon-si (KR)

(72) Inventors: Jae Wook Shim, Icheon-si (KR); Hyun Seok Moon, Hwaseong-si (KR); Jong Keun Song, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 16/995,306

(22) Filed: Aug. 17, 2020

(65) Prior Publication Data

US 2021/0255092 A1    Aug. 19, 2021

(30) Foreign Application Priority Data

Feb. 17, 2020    (KR) .................. 10-2020-0019096

(51) Int. Cl.
*G01N 21/17*    (2006.01)
*G01N 21/49*    (2006.01)
(Continued)

(52) U.S. Cl.
CPC ....... *G01N 21/1702* (2013.01); *A61B 5/0048* (2013.01); *A61B 5/0059* (2013.01);
(Continued)

(58) Field of Classification Search
CPC .............. G01N 21/1702; G01N 21/49; G01N 21/1717; G01N 21/4795;
(Continued)

(56) References Cited

U.S. PATENT DOCUMENTS

| 6,979,292 B2 | 12/2005 | Kanayama et al. |
| 8,103,329 B2 | 1/2012 | Fomitchov et al. |

(Continued)

FOREIGN PATENT DOCUMENTS

| JP | 11153666 A | 6/1999 |
| JP | 4809685 B2 | 11/2011 |

(Continued)

OTHER PUBLICATIONS

Lev, A., and B. G. Sfez. "Pulsed ultrasound-modulated light tomography." Optics Letters 28.17 (2003): 1549-1551. (Year: 2003).*

(Continued)

*Primary Examiner* — Dominic J Bologna
(74) *Attorney, Agent, or Firm* — Sughrue Mion, PLLC

(57) ABSTRACT

Provided is an apparatus configured to analyze a component of an object, the apparatus including a signal detection sensor including a light source configured to emit light to the object, a detector configured to detect a signal of light scattered or reflected from the object, an ultrasonic generator configured to transmit an ultrasonic wave toward the object at irregular ultrasonic transmission time intervals to modulate a frequency of the light emitted to the object, and a controller configured to control the ultrasonic transmission time intervals of the ultrasonic generator to be irregular, and a processor configured to control the signal detection sensor and analyze the component of the object based on the signal of light detected by the detector.

18 Claims, 6 Drawing Sheets

(51) Int. Cl.
*G01N 21/47* (2006.01)
*A61B 5/145* (2006.01)
*A61B 5/00* (2006.01)
*A61B 5/1455* (2006.01)

(52) U.S. Cl.
CPC .......... *A61B 5/0097* (2013.01); *A61B 5/1455* (2013.01); *A61B 5/14532* (2013.01); *G01N 21/1717* (2013.01); *G01N 21/4795* (2013.01); *G01N 21/49* (2013.01); *G01N 2021/1706* (2013.01)

(58) Field of Classification Search
CPC .......... G01N 2021/1706; A61B 5/0059; A61B 5/1455; A61B 5/14532; A61B 5/0048; A61B 5/0097
See application file for complete search history.

(56) References Cited

U.S. PATENT DOCUMENTS

| | | |
|---|---|---|
| 8,364,414 B2 | 1/2013 | Masumura |
| 2007/0187632 A1 | 8/2007 | Igarashi |
| 2008/0296514 A1* | 12/2008 | Metzger ............ G01N 21/4795 250/492.1 |
| 2012/0197133 A1 | 8/2012 | McKenna et al. |
| 2017/0181633 A1 | 6/2017 | Herrmann |
| 2018/0317822 A1 | 11/2018 | Herrmann |
| 2019/0082964 A1 | 3/2019 | Byrnes et al. |

FOREIGN PATENT DOCUMENTS

| | | |
|---|---|---|
| JP | 5815243 B2 | 11/2015 |
| KR | 101583302 B1 | 1/2016 |

OTHER PUBLICATIONS

Communication dated Mar. 1, 2021, issued by the European Patent Office in counterpart European Application No. 20193689.5.

A. Lev et al., "Pulsed ultrasound-modulated light tomography," Optical Society of America, Optics Letters, vol. 28, No. 17, Sep. 2003, pp. 1549-1551.

\* cited by examiner

SIGNAL DETECTION SENSOR, APPARATUS AND METHOD FOR ANALYZING COMPONENT OF OBJECT

CROSS-REFERENCE TO RELATED APPLICATION

This application claims priority from Korean Patent Application No. 10-2020-0019096, filed on Feb. 17, 2020, in the Korean Intellectual Property Office, the entire disclosure of which is incorporated herein by reference.

BACKGROUND

1. Field

Example embodiments of the present disclosure relate to a signal detection sensor coupled to an ultrasonic generator and a method for analyzing components of an object using the signal detection sensor.

2. Description of Related Art

Recently, technologies using optical sensors have been developed in various fields, such as non-invasive monitoring of human diseases. For example, diabetes is a chronic disease that causes various complications and is difficult to cure, and hence people with diabetes are advised to check their blood glucose regularly to prevent complications. Especially, when insulin is administered to control blood glucose, the blood glucose levels may have to be closely monitored to avoid hypoglycemia and control insulin dosage. In general, noninvasive methods are easier to diagnose than invasive methods, but accuracy may be reduced. Research on technology for improving accuracy of noninvasive methods by combining an optical sensor with an ultrasonic wave transmitter device has been conducted.

SUMMARY

According to an aspect of an example embodiment, there is provided an apparatus configured to analyze a component of an object, the apparatus including a signal detection sensor including a light source configured to emit light to the object, a detector configured to detect a signal of light scattered or reflected from the object, an ultrasonic generator configured to transmit an ultrasonic wave toward the object at irregular ultrasonic transmission time intervals to modulate a frequency of the light emitted to the object, and a controller configured to control the ultrasonic transmission time intervals of the ultrasonic generator to be irregular, and a processor configured to control the signal detection sensor and analyze the component of the object based on the signal of light detected by the detector.

The controller may be further configured to gradually increase or decrease the ultrasonic transmission time intervals based on an order of ultrasonic transmission of the ultrasonic generator or assign some of a plurality of predefined different time intervals to the ultrasonic transmission time intervals based on a pseudo random sequence.

The controller may be further configured to control a difference between an ith transmission time interval $T_i$ and an (i+1)th transmission time interval $T_{i+1}$ to be greater than a predetermined threshold, where i is an integer greater than or equal to 1.

The predetermined threshold may be greater than a length of an ultrasonic transmission wave of the ultrasonic generator.

The predetermined threshold may be greater than a length of time for which a main reflected wave for an ultrasonic transmission wave of the ultrasonic generator is received by the detector.

The controller may be further configured to control a difference $T_i - T_j$ between an ith transmission time interval $T_i$ and a jth transmission time interval $T_j$ to be equal to a product of a predetermined threshold and a difference i−j between i and j, where i is an integer greater than or equal to 1, and j is an integer greater than or equal to 1 and is not equal to i.

The controller may be further configured to select two or more time intervals from among a plurality of predefined different time intervals and repeatedly assign the two or more selected time intervals to the ultrasonic transmission time intervals.

The controller may be further configured to select two or more time intervals having values consecutive to each other from among the plurality of predefined different time intervals.

The processor may be further configured to extract second signals of a plurality of time intervals from a first signal detected by the detector, ensemble average the extracted second signals, and analyze the component of the object based on an ensemble average result.

The processor may be further configured to extract, from the first signal, the second signals of same time intervals based on a transmission time point of each ultrasonic wave.

The processor may be further configured to detect, from the ensemble average result, a time interval in which a main light signal is received based on a signal intensity, and analyze the component of the object based on a signal of the detected time interval.

The processor may be further configured to detect a time interval in which the signal intensity is greatest from among remaining time intervals, except for signals of ultrasonic transmission intervals in the ensemble average result, as a time interval in which the main light signal is received.

The component of the object may include one or more of blood sugar, triglycerides, cholesterol, calories, protein, antioxidant related components, carotenoids, lactate, and uric acid.

According to another aspect of an example embodiment, there is provided a method of analyzing a component of an object, including emitting light to the object, transmitting an ultrasonic wave toward the object at irregular ultrasonic transmission time intervals, detecting a signal of light scattered or reflected from the object, a frequency of the signal of light being modulated by the ultrasonic wave, and analyzing the component of the object based on the detected signal of light.

The transmitting of the ultrasonic wave may include gradually increasing or decreasing time intervals based on an order of ultrasonic transmission of an ultrasonic generator or assigning some of a plurality of predefined different time intervals to the ultrasonic transmission time intervals based on a pseudo random sequence.

The transmitting of the ultrasonic wave may include selecting two or more time intervals from among a plurality of predefined different time intervals and repeatedly assigning the two or more selected time intervals to the ultrasonic transmission time intervals.

The analyzing of the component of the object may include extracting second signals of a plurality of time intervals from a first signal detected in the detecting of the signal of light, ensemble averaging the extracted second signals, and analyzing the component of the object based on an ensemble average result.

The analyzing of the component of the object may include detecting, from the ensemble average result, a time interval in which a main light signal is received on the basis of a signal intensity, and analyzing the component of the object based on a signal of the detected time interval.

According to another aspect of an example embodiment, there is provided a signal detection sensor including a light source configured to emit light to an object, a detector configured to detect a light signal scattered or reflected from the object, an ultrasonic generator configured to modulate the light signal by transmitting an ultrasonic wave to the object in a direction different from a direction in which the light is emitted to the object, and a controller configured to control ultrasonic transmission time intervals of the ultrasonic generator to be irregular.

The controller may be further configured to gradually increase or decrease time intervals based on an order of ultrasonic transmission of the ultrasonic generator, assign some of a plurality of predefined different time intervals to the ultrasonic transmission time intervals based on a pseudo random sequence, or select two or more time intervals from among the plurality of predefined different time intervals and repeatedly assign the two or more selected time intervals to the ultrasonic transmission time intervals

BRIEF DESCRIPTION OF THE DRAWINGS

The above and/or other aspects, features, and advantages of example embodiments will be more apparent from the following description taken in conjunction with the accompanying drawings, in which.

DETAILED DESCRIPTION

Figure 1:
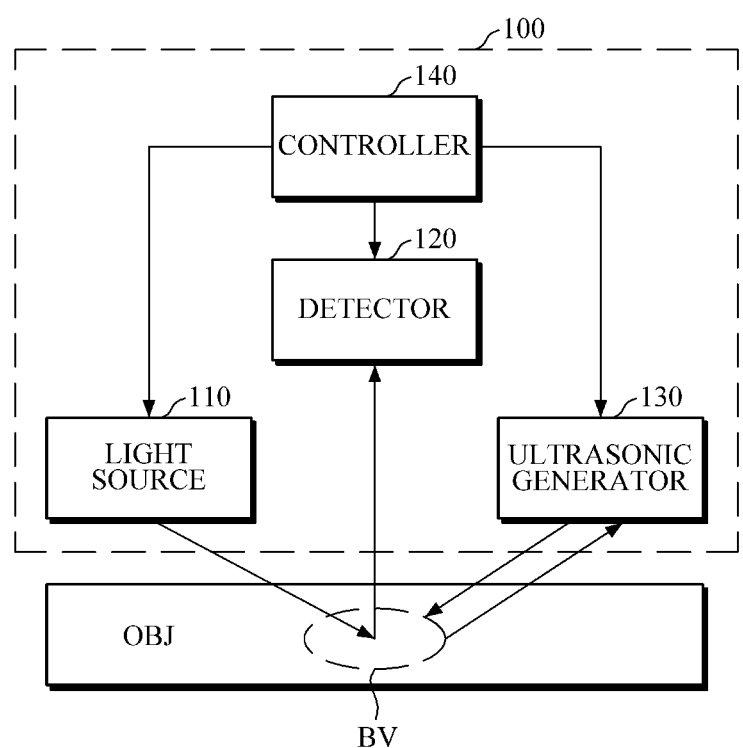
FIG. 1 is a block diagram illustrating a signal detection sensor according to an example embodiment.

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the example embodiments set forth herein. Rather, these example embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, example embodiments of a signal detection sensor and an apparatus and method for analyzing a component of an object will be described in detail with reference to the drawings.

FIG. 1 is a block diagram illustrating a signal detection sensor according to an example embodiment.

The signal detection sensor 100 according to an example embodiment may be a sensor that detects a signal of light scattered or reflected from an object and may be mounted as a module in a device that analyzes a component of the object using the signal of light. The signal detection sensor 100 may be formed as a separate sensor device and may be electrically connected to the device for analyzing the component of the object or connected through wireless communication.

Referring to FIG. 1, the signal detection sensor 100 may include a light source 110, a detector 120, an ultrasonic generator 130, and a controller 140.

The light source 110 emits light of one or more wavelengths to the object OBJ. The light source 110 may include a light emitting diode (LED), a laser diode, a phosphor, and the like, but is not limited thereto. For example, the light source 110 may be formed of a single LED to irradiate the object with light of one or more wavelengths in a time division manner. The light source 110 may be formed of a plurality LED arrays and each LED may emit light of the same wavelength or a different wavelength.

The detector 120 detects scattered or reflected light when light emitted to the object OBJ by the light source 110 is scattered or reflected from the object OBJ. The detector 120 may include a photodiode, a photo transistor, or an image sensor. However, embodiments are not limited thereto. For example, the detector 120 may be formed of a single photodiode or a plurality of photodiode arrays. The detector 120 may output a signal of the detected light as an electrical signal.

The ultrasonic generator 130 may transmit ultrasonic waves toward a measurement area of the object 130 and transmit ultrasonic waves toward the object OBJ in a direction different from a light emission direction of the light source 110. The ultrasonic generator 130 may be an ultrasonic transducer. However, the types of communication are not limited to the above examples. The ultrasonic generator 130 may transmit ultrasonic waves of a predetermined frequency under the control of the controller 140, and the ultrasonic waves may converge on the measurement area BV in the object OBJ.

The light emitted by the light source 110 may interact with the ultrasonic waves in the measurement area BV in the object OBJ, so that optical properties, for example, scattering or reflecting ability of light, may be changed. That is, a frequency of the light signal emitted by the light source 110 and scattered or reflected from the measurement area BV may be demodulated by the frequency of the ultrasonic waves and be detected by the detector 120. Thus, the position of the measurement area BV may be more efficiently searched to more accurately analyze a component of the object.

The controller 140 may be electrically connected to the light source 110, the detector 120, and/or the ultrasonic generator 130. The controller 140 may drive the light source 110 to continuously emit light of a predetermined wavelength toward the measurement area BV of the object OBJ for a predetermined period of time. Also, the controller 140 may control the ultrasonic generator 130 to emit ultrasonic waves toward the object OBJ. Meanwhile, the controller 140 may adjust an emission direction of the light source 110 and/or the ultrasonic generator 130 such that the light and the ultrasonic waves can converge on the measurement area BV of the object OBJ.

The light emitted by the light source 110 has a frequency modulated to the ultrasonic wave in the measurement area BV of the object OBJ, and the scattered or reflected light signal whose frequency is modulated is detected by the detector 120. The detector 120 may output a signal of the detected light to an apparatus for analyzing a component of an object, and the apparatus for analyzing a component of an object may analyze components of the object through an analysis of a frequency of a light signal.

Figure 2A:
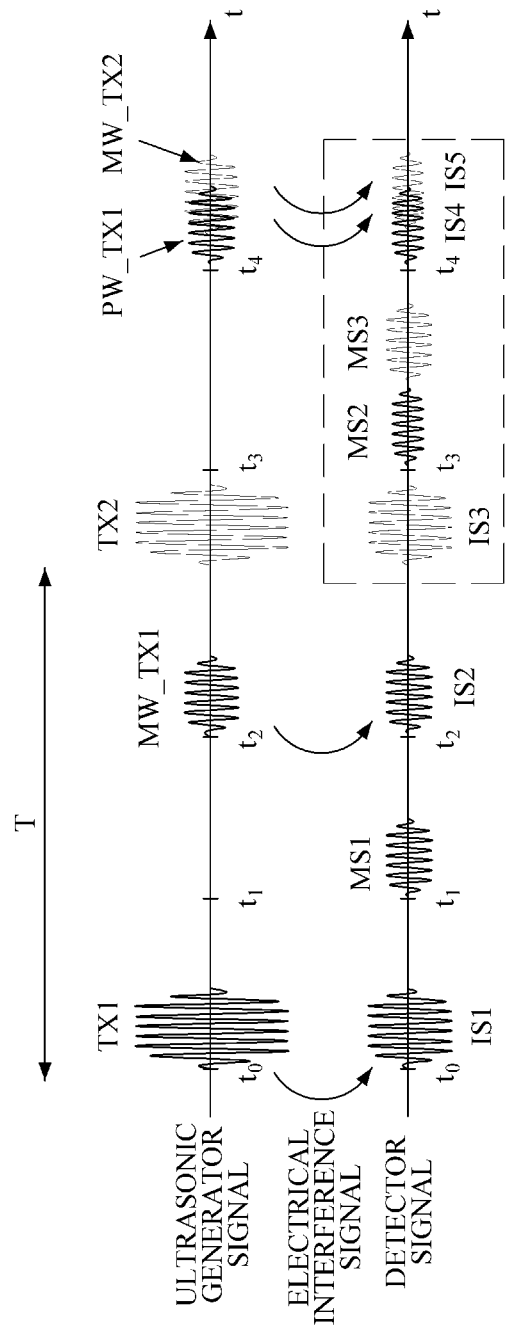
FIGS. 2A and 2B are diagrams for describing a method of driving a ultrasonic generator.
Figure 2B:
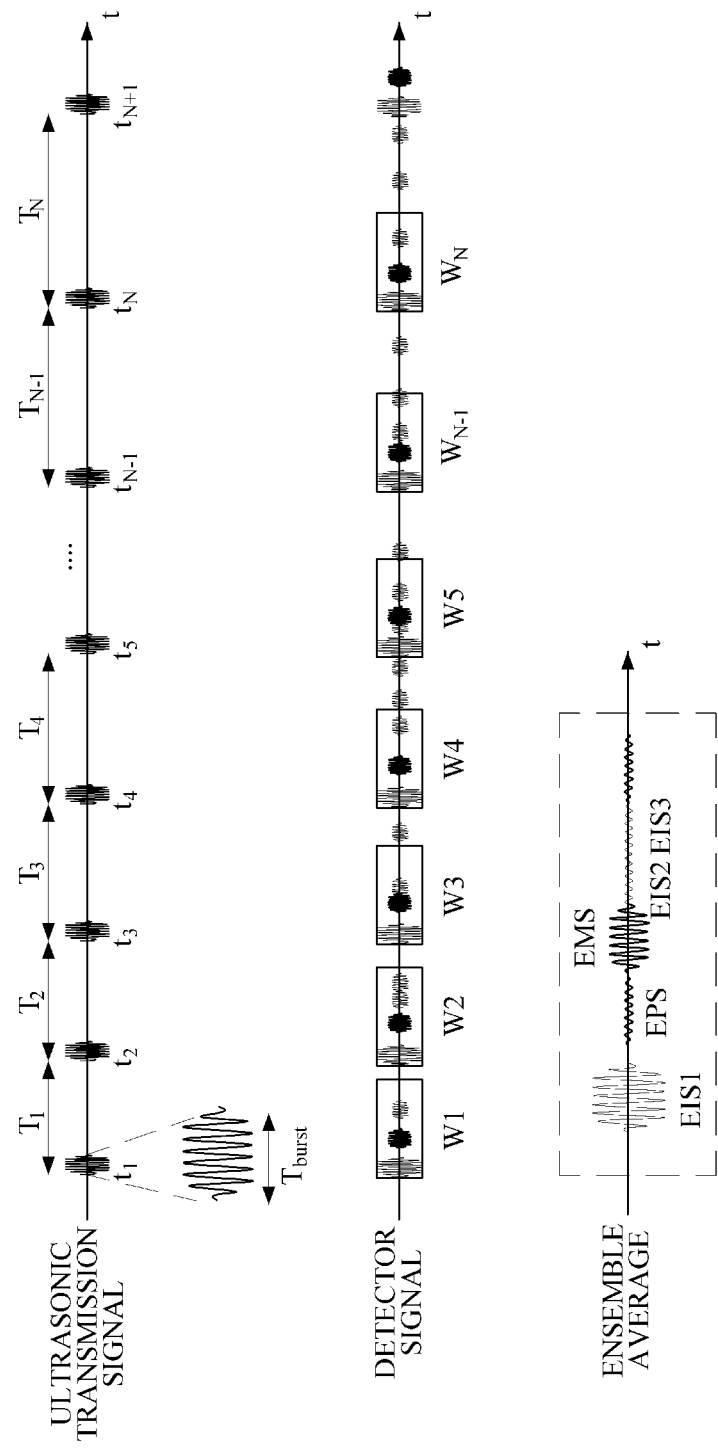

FIGS. 2A and 2B are diagrams for describing a method of driving an ultrasonic generator.

For example, when a component of an object is analyzed, the component of the object may be analyzed by measuring a signal a plurality of times for a predetermined period of time and overlapping the measured signals in order to improve a signal-to-noise ratio.

Referring to FIG. 2A, in general, a plurality of ultrasonic waves TX1 and TX2 may be transmitted at uniform time intervals by setting an ultrasonic transmitting period T of the ultrasonic generator 130 to be constant. In this case, various reflected waves for the ultrasonic waves exist in the measurement area BV of the object OBJ, and the reflected waves affect, as interference signals, light signals to be measured.

For example, as shown in FIG. 2A, a first light signal MS1, a second light signal MS2, and a third light signal MS3 may be detected by the detector 120. In this case, the second light signal MS2 may be modulated by a parasitic reflected wave of a first ultrasonic wave TX1 and the third light signal MS3 may be modulated by a main reflected wave of a second ultrasonic wave TX2. Further, electrical interference signals IS1 and IS3 by the first ultrasonic wave TX1 and the second ultrasonic wave TX2, an interference signal IS2 by the main reflected wave MW_TX1 of the first ultrasonic wave TX1, an interference signal IS5 by a main reflected wave MW_TX2 of the second ultrasonic wave TX2, an interference signal IS4 by the parasitic reflected wave PW_TX1 of the first ultrasonic wave TX1, and the like may be detected by the detector 120.

As such, the signals detected for a predetermined period of time by the detector include various interference signals besides main light signals scattered or reflected from the measurement area, and the interference signals affect the intensity of the main light signals, thereby affecting the accuracy of component analysis of the object. For example, when a method in which light signals are overlapped through repeated measurement of the light signal in order to improve the signal-to-noise ratio is employed, it is difficult to distinguish the main light signal from various interference signals, which hinders extraction of the main light signal necessary for component analysis of the object. Thus, the accuracy of the object component analysis may be reduced.

According to the example embodiment, the controller 140 may adjust the ultrasonic transmission period of the ultrasonic generator 130 to be irregular so as to increase the accuracy of the method of analyzing the component of the object by repeatedly measuring the light signal and overlapping the detected light signals.

Referring to FIG. 2B, when a signal is detected N times and the detected signals are overlapped, the controller 140 may control the ultrasonic transmitter 130 to transmit an ultrasonic wave at a plurality of time points $t_1$, $t_2$, $t_3$, $t_4$, $t_5$, . . . , $t_{N-1}$, and $t_N$. The controller 140 may adjust N ultrasonic transmission time intervals $T_1$, $T_2$, $T_3$, $T_4$, . . . , $T_{N-1}$, and $T_N$ to be irregular.

For example, the controller 140 may control the ultrasonic transmission time intervals to be gradually increased or decreased in the order of the ultrasonic transmission times. In this case, each of the ultrasonic transmission time intervals $T_1$, $T_2$, $T_3$, $T_4$, . . . , $T_{N-1}$, and $T_N$ may be controlled to have a value greater than a predetermined threshold $T_{min}$. For example, the predetermined threshold $T_{min}$ may be set to have a value greater than a length of time for which a main reflected wave of an ultrasonic transmission signal is received at an ultrasonic receiving end.

For example, the controller 140 may control a difference $D_i$ between the ith (i is an integer greater than or equal to 1) transmission time interval $T_i$ and the (i+1)th transmission time interval $T_{i+1}$ to be greater than a predetermined threshold $D_{min}$. In this case, the predetermined threshold $D_{min}$ may be set to have a value greater than a length $T_{burst}$ of an ultrasonic transmission wave.

The controller 140 may control the ultrasonic transmission time interval to be gradually increased or decreased, and may gradually increase or decrease a degree of increase or decrease in the ultrasonic transmission time interval. For example, each of a first ultrasonic transmission time interval $T_1$, a second ultrasonic transmission time interval $T_2$, and a third ultrasonic transmission time interval $T_3$ may be set to 1, 2, and 4, thereby gradually increasing the degree of increase in the ultrasonic transmission time interval. In this case, the degree of increase or decrease in the ultrasonic transmission time interval may be set in advance.

According to an example embodiment, the control unit 140 may control the ultrasonic transmission time interval to be gradually increased or decreased in the order of the ultrasonic transmission times, but maintain the same degree of increase or decrease in the ultrasonic transmission time interval. For example, a difference $T_j-T_i$ between the ith transmission time interval $T_i$ and the jth (j is an integer greater than or equal to 1) transmission time interval may be controlled to be equal to the product of a predetermined threshold D and a difference i–j between i and j. In this case, the predetermined threshold D may be set in advance.

In another example, the controller 140 may randomly assign some of a plurality of predefined different time intervals to the respective ultrasonic transmission time intervals using a pseudo random sequence. For example, as described above, a plurality of time intervals may be predefined so as to gradually increase or decrease in the order of the ultrasonic transmission times. The controller 140 may allow an ultrasonic wave to be transmitted at irregular time intervals having no predetermined pattern by randomly assigning values of the plurality of predefined different time intervals to the respective ultrasonic transmission time intervals.

As another example, the controller 140 may select two or more time intervals from among values of the plurality of predefined different time intervals, and repeatedly assign the selected time intervals to the ultrasonic transmission time intervals. For example, a set of values of the plurality of different time intervals $\{T_1, T_2, T_3, T_4, T_5, \ldots, \text{and } T_N\}$ is predefined, the controller 140 may select two or more consecutive values (e.g., $T_1$, $T_2$, and $T_3$) or two or more non-consecutive values (e.g., $T_1$, $T_3$, and $T_N$) from among the values, and repeatedly assign the selected values to the ultrasonic transmission time intervals.

Various example embodiments of controlling the ultrasonic transmission time intervals to be irregular have been described above. However, the embodiments are not limited to the above examples and may be modified in various other ways.

Referring again to FIG. 2B, when the signals detected by the detector are overlapped in predetermined time units W1, W2, W3, W5, WN−1, and WN and ensemble-averaged, a main light receiving signal EMS and an interference signal EIS1 by an ultrasonic transmission signal may increase in their intensity and a light receiving signal EPS and the other interference signals EIS2 and EIS3 by the other parasitic reflected waves do not overlap or overlap to a small extent, and thus the signal intensity is detected to be relatively weak. Therefore, the signal-to-noise ratio of the main light receiving signal may be improved, and thereby it is possible to accurately detect the timing of occurrence of the main light signal, and it is possible to improve the accuracy by analyzing a component of the object using the main light receiving signal measured at a correct position.

Figure 3:
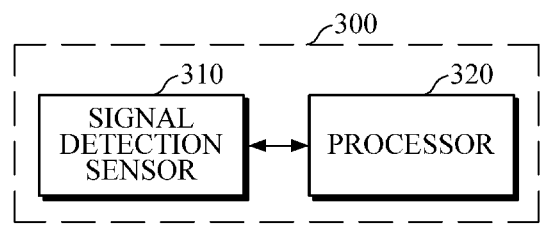
FIG. 3 is a block diagram illustrating an apparatus for analyzing a component of an object according to an example embodiment.

FIG. 3 is a block diagram illustrating an apparatus for analyzing a component of an object according to an example embodiment.

The apparatus 300 for analyzing a component according to the example embodiment may include the above-described signal detection sensor 100 or a module separately fabricated to implement various functions of the signal detection sensor 100. The apparatus 300 for analyzing a component may be manufactured in a small size and mounted in a wearable device that can be worn on a wrist of a user or in a smart device that can be carried by the user, and be used in noninvasively analyzing a component. However, embodiments are not limited thereto, and the apparatus 300 for analyzing a component may be mounted in a noninvasive or in-vivo analysis device that can be used in a medical institution for diagnosing and studying a human disease through analysis of a light signal. The apparatus 300 for analyzing a component may be mounted in an analysis device used in various fields that utilize a light signal other than a device for component analysis of a living body.

Referring to FIG. 3, the apparatus 300 for analyzing a component may include a signal detection sensor 310 and a processor 320 according to an example embodiment.

The signal detection sensor 310 may include a light source and a detector. The light source and the detector may perform light signal detection for component analysis of an object. In this case, the object may be a biological tissue, such as a skin tissue of a human body, but is not limited thereto, and may include objects that may utilize other light signal analysis. Hereinafter, a biological tissue, such as human skin, will be described as an example for convenience of description.

For example, the light source may be formed of one or more LEDs and may emit light in a direction of a blood vessel of the object. The detector may be formed of one or more photodiodes and the like and may detect a light signal that is scattered or reflected from a blood vessel wall or inside the blood vessel of the object or is scattered or reflected by other components in the biological tissue.

Also, the signal detection sensor 310 may further include an ultrasonic generator that transmits an ultrasonic wave to a measurement area in order to modulate the light signal emitted by the light source. A location of the measurement area, for example, a depth of a blood vessel, may be specified using the ultrasonic wave. The ultrasonic generator may transmit a plurality of ultrasonic waves having a predetermined frequency a plurality of times. In this case, the ultrasonic generator may transmit ultrasonic waves at irregular time intervals.

The light emitted by the light source interacts with the ultrasonic waves and, in turn, the frequency is modulated. For example, the frequency of the light emitted by the light source may be reflected by the blood vessel wall and modulated to a first frequency. In addition, the light entering the blood vessel may be Doppler-shifted with respect to the frequency of the ultrasonic waves by the Doppler effect in the flowing blood, and be modulated to a second frequency. As such, the frequency-modulated light signals may be detected by the detector. The detector may convert the detected light signal into an electrical signal and transmit the electrical signal to the processor 320.

In addition, the signal detection sensor 310 may further include a controller that controls a time interval at which ultrasonic waves are transmitted to be irregular. The controller may be integrated with the processor 320. For example, the controller may gradually increase or decrease a ultrasonic transmission time interval. In this case, a degree of increase or decrease in each ultrasonic transmission time interval may be identical to or different from each other. In another example, the controller may randomly assign values of a plurality of predefined different time intervals to each ultrasonic transmission time interval. According to an example embodiment, values of two or more any time intervals are selected from among a plurality of different time intervals and the selected values may be repeatedly assigned. These examples have been described with reference to FIGS. 1 to 2B, and thus detailed descriptions thereof will not be reiterated.

The processor 320 may analyze a component of the object using a signal received from the detector of the signal detection sensor 310. For example, a component of the subject may include, but is not limited to, one or more of blood sugar, triglycerides, cholesterol, calories, protein, antioxidant related components, carotenoids, lactate, and uric acid.

For example, the processor 320 may extract second signals of a plurality of time intervals from a first signal detected by the detector and analyze the component of the object by ensemble averaging the extracted second signals. For example, as illustrated in FIG. 2B, the processor 320 may ensemble average windows of the same time intervals based on the transmission time point of each ultrasonic wave in the first signal, and extract a main light signal from a signal obtained through the ensemble average.

The processor 320 may extract the main light signal from the ensemble-averaged signal on the basis of the signal intensity. For example, the processor 320 may extract a signal of a time interval in which the signal intensity is the greatest as the main light signal, except for signals at the time of transmitting the ultrasonic waves. When the ensemble average is made by setting ultrasonic transmission time intervals to be irregular, the main light signals are overlapped and thus the intensity of the main light signal is increased, while the intensity of the remaining interference signals is relatively decreased. Therefore, it is possible to relatively accurately specify a reception time point of the main light signal.

The processor 320 may analyze the component of the object using the detected main light signal. For example, the component may be estimated using a component estimation model that defines a correlation between the intensity of the main optical light signal and the component to be analyzed. However, embodiments are not limited thereto, and various known component analysis techniques may be used.

Thus, by more accurately extracting the main light signal whose frequency is modulated by the ultrasonic wave, the signal of the light scattered or reflected from the measurement area to be analyzed may be utilized for component analysis, thereby improving component analysis performance.

Figure 4:
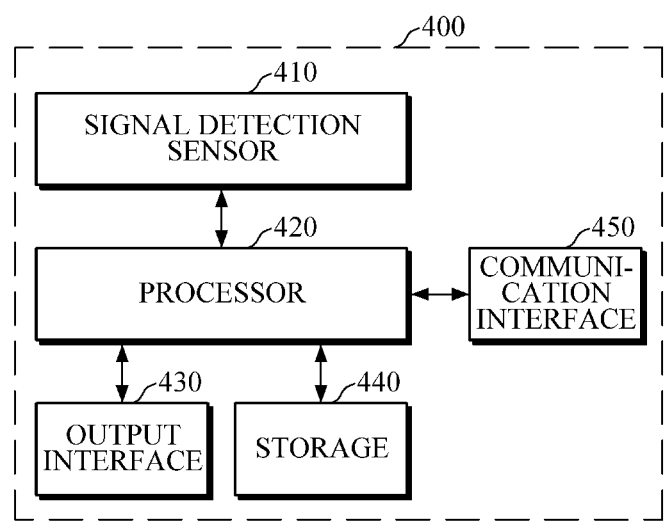
FIG. 4 is a block diagram illustrating an apparatus for analyzing a component of an object according to another example embodiment.

FIG. 4 is a block diagram illustrating an apparatus for analyzing a component of an object according to another example embodiment.

Referring to FIG. 4, an apparatus 400 for analyzing a component may include a signal detection sensor 410, a processor 420, an output interface 430, a storage 440, and a communication interface 450. Configurations of the signal detection sensor 410 and the processor 420 are described in detail above, and thus descriptions thereof will be omitted.

The output interface 430 may output a processing result of the processor 120 and provide the same to a user. For example, a component analysis result of the object may be provided to the user by using a visual output module, such as a display, a voice output module, such as a speaker, or a haptic module that provides information by vibration or tactile sensation. In addition, a health condition of the user may be monitored based on the component analysis result, and a warning may be output when a risk of the health condition is expected.

The storage 440 may store a variety of information required for component analysis of the object or a processing result of the processor 420. For example, reference information may include information on driving of the signal detection sensor, such as a light source driving condition or an ultrasonic wave generation frequency, an estimation model required for component analysis of the object, and the like. The information may include information on a user's personal characteristics, such as health status, age, gender, and the like of the user. However, the information is not limited to the above examples.

The storage unit 440 may include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

The communication interface 450 may communicate with an external device to transmit and receive data on signal detection and component analysis of the object. In this case, the external device may include a user's portable device, such as a smartphone, a tablet personal computer (PC), a desktop PC, a notebook PC, and the like, or a device used in a professional medical institution. The communication interface 450 may use Bluetooth communication, Bluetooth low energy (BLE) communication, near field communication unit, wireless local access network (WLAN) communication, Zigbee communication, infrared data association (IrDA) communication, Wi-Fi direct (WFD) communication, ultra wideband (UWB) communication, Ant+ communication, Wi-Fi communication, and 3G, 4G, and 5G communication technologies. However, the types of communication are not limited to the above examples.

Figure 5:
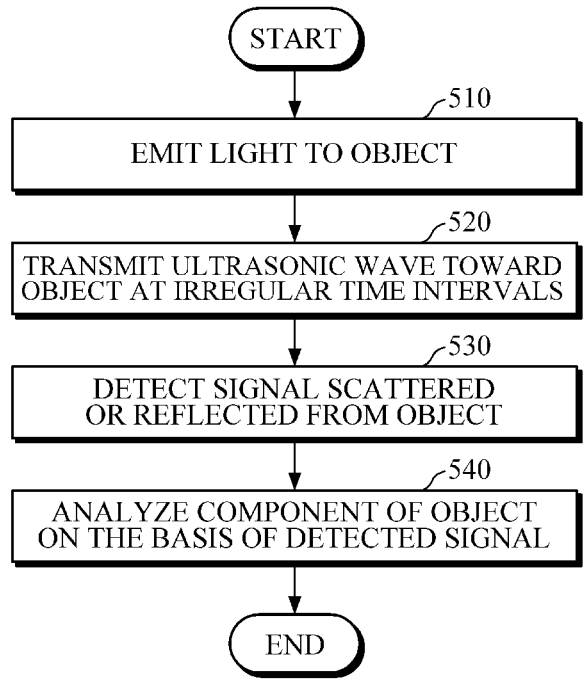
FIG. 5 is a flowchart illustrating a method of analyzing a component of an object according to an example embodiment.

FIG. 5 is a flowchart illustrating a method of analyzing a component of an object according to an example embodiment. The method of FIG. 5 may be an example embodiment of a component analysis method performed by the apparatus 300 for analyzing a component as illustrated in FIG. 3 or apparatus 400 for analyzing a component as illustrated in FIG. 4.

The apparatus 300 or 400 for analyzing a component may emit light toward an object in operation 510. When a request for analyzing a component of the object is received from a user or an external device, the apparatus 300 or 400 for analyzing a component may drive a light source to continuously emit light of a predetermined wavelength for a predetermined time.

Then, an ultrasonic wave may be transmitted toward the object a plurality of times using an ultrasonic generator in operation 520. At this time, ultrasonic transmission time intervals may be set to be irregular. For example, the ultrasonic transmission time intervals may be gradually increased or decreased, or predefined different time intervals may be randomly assigned to the respective ultrasonic transmission times. According to an example embodiment, two or more different time intervals may be repeatedly assigned.

In this case, the order of operations 510 and 520 is not clearly specified. For example, an ultrasonic wave may be first transmitted to specify an area to be measured in the object and then light may be emitted to the corresponding measurement area.

Thereafter, a returning light signal scattered or reflected from the object may be detected by a detector in operation 530. The light emitted to the measurement area of the object interacts with the ultrasonic wave at the measurement area of the object and is, in turn, modulated. For example, the light may be Doppler-shifted and modulated by the Doppler effect according to a blood flow in a blood vessel. Thus, by detecting the light whose frequency is modulated by the Doppler effect, it is possible to more accurately detect a light signal of the desired measurement area.

Then, a component may be analyzed using the light signal detected in operation 530 in operation 540. A main light signal may be extracted by making an ensemble average over predetermined time interval units from a signal detected for a predetermined period of time by the detector. By making the ultrasonic transmission time intervals irregular, the overlapping width of surrounding interference signals is relatively reduced compared to the overlap of the main light signals, and hence by using such a characteristic, it is possible to more accurately detect a time point at which the main light signal is received. For example, a signal at a position at which the signal intensity is the greatest, except for an interference signal at the time of transmitting an ultrasonic wave, or a signal at a position at which the signal intensity is greater by a predetermined threshold than the intensity of signals at different time points may be obtained as a main light signal. In this case, the obtained main light signal is a light signal scattered or reflected in a blood vessel of interest and thus it is possible to more accurately estimate a component of the blood vessel of interest.

The example embodiments can be implemented as computer readable codes in a computer readable record medium.

The computer readable record medium includes all types of record media in which computer readable data read by a computer system are stored.

Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner. Further, functional programs, codes, and code segments for implementing the embodiments can be easily inferred by a skilled computer programmer in the art.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents.

While example embodiments have been described with reference to the figures, it will be understood by those of ordinary skill in the art that various changes in form and details may be made therein without departing from the spirit and scope as defined by the following claims.

What is claimed is:

1. An apparatus configured to analyze a component of an object, the apparatus comprising:
    a signal detection sensor comprising:
        a light source configured to emit light to the object,
        a detector configured to detect a signal of light scattered or reflected from the object,
        an ultrasonic generator configured to transmit an ultrasonic wave toward the object at irregular ultrasonic transmission time intervals to modulate a frequency of the light emitted to the object, and
        a controller configured to control the ultrasonic transmission time intervals of the ultrasonic generator to be irregular; and
    a processor configured to control the signal detection sensor and analyze the component of the object based on the signal of light detected by the detector,
    wherein the controller is further configured to gradually increase or decrease the ultrasonic transmission time intervals based on an order of ultrasonic transmission of the ultrasonic generator or assign some of a plurality of predefined different time intervals to the ultrasonic transmission time intervals based on a pseudo random sequence.

2. The apparatus of claim 1, wherein the controller is further configured to control a difference between an ith transmission time interval Ti and an (i+1)th transmission time interval Ti+1 to be greater than a predetermined threshold, where i is an integer greater than or equal to 1.

3. The apparatus of claim 2, wherein the predetermined threshold is greater than a length of an ultrasonic transmission wave of the ultrasonic generator.

4. The apparatus of claim 2, wherein the predetermined threshold is greater than a length of time for which a main reflected wave for an ultrasonic transmission wave of the ultrasonic generator is received by the detector.

5. The apparatus of claim 1, wherein the controller is further configured to control a difference Ti−Tj between an ith transmission time interval Ti and a jth transmission time interval Tj to be equal to a product of a predetermined threshold and a difference i−j between i and j,
    where i is an integer greater than or equal to 1, and j is an integer greater than or equal to 1 and is not equal to i.

6. The apparatus of claim 1, wherein the controller is further configured to select two or more time intervals from among the plurality of predefined different time intervals and repeatedly assign the two or more selected time intervals to the ultrasonic transmission time intervals.

7. The apparatus of claim 6, wherein the controller is further configured to select two or more time intervals having values consecutive to each other from among the plurality of predefined different time intervals.

8. The apparatus of claim 1, wherein the processor is further configured to extract second signals of a plurality of time intervals from a first signal detected by the detector, ensemble average the extracted second signals, and analyze the component of the object based on an ensemble average result.

9. The apparatus of claim 8, wherein the processor is further configured to extract, from the first signal, the second signals of same time intervals based on a transmission time point of each ultrasonic wave.

10. The apparatus of claim 8, wherein the processor is further configured to detect, from the ensemble average result, a time interval in which a main light signal is received based on a signal intensity, and analyze the component of the object based on a signal of the detected time interval.

11. The apparatus of claim 10, wherein the processor is further configured to detect a time interval in which the signal intensity is greatest from among remaining time intervals, except for signals of ultrasonic transmission intervals in the ensemble average result, as a time interval in which the main light signal is received.

12. The apparatus of claim 1, wherein the component of the object comprises one or more of blood sugar, triglycerides, cholesterol, calories, protein, antioxidant related components, carotenoids, lactate, and uric acid.

13. A method of analyzing a component of an object, comprising:
    emitting light to the object;
    transmitting an ultrasonic wave toward the object at irregular ultrasonic transmission time intervals;
    detecting a signal of light scattered or reflected from the object, a frequency of the signal of light being modulated by the ultrasonic wave; and
    analyzing the component of the object based on the detected signal of light,
    wherein the transmitting of the ultrasonic wave comprises gradually increasing or decreasing time intervals based on an order of ultrasonic transmission of an ultrasonic generator or assigning some of a plurality of predefined different time intervals to the ultrasonic transmission time intervals based on a pseudo random sequence.

14. The method of claim 13, wherein the transmitting of the ultrasonic wave comprises selecting two or more time intervals from among the plurality of predefined different time intervals and repeatedly assigning the two or more selected time intervals to the ultrasonic transmission time intervals.

15. The method of claim 13, wherein the analyzing of the component of the object comprises:
    extracting second signals of a plurality of time intervals from a first signal detected in the detecting of the signal of light, ensemble averaging the extracted second signals, and
analyzing the component of the object based on an ensemble average result.

16. The method of claim 15, wherein the analyzing of the component of the object comprises detecting, from the ensemble average result, a time interval in which a main light signal is received on the basis of a signal intensity, and analyzing the component of the object based on a signal of the detected time interval.

17. A signal detection sensor comprising:
- a light source configured to emit light to an object;
- a detector configured to detect a light signal scattered or reflected from the object;
- an ultrasonic generator configured to modulate the light signal by transmitting an ultrasonic wave to the object in a direction different from a direction in which the light is emitted to the object; and
- a controller configured to control ultrasonic transmission time intervals of the ultrasonic generator to be irregular,
- wherein the controller is further configured to gradually increase or decrease time intervals based on an order of ultrasonic transmission of the ultrasonic generator or assign some of a plurality of predefined different time intervals to the ultrasonic transmission time intervals based on a pseudo random sequence.

18. The signal detection sensor of claim 17, wherein the controller is further configured to select two or more time intervals from among the plurality of predefined different time intervals and repeatedly assign the two or more selected time intervals to the ultrasonic transmission time intervals.

* * * * *